United States Patent
Wennek

(10) Patent No.: US 6,540,718 B1
(45) Date of Patent: Apr. 1, 2003

(54) APPLIANCE FOR RINSING

(76) Inventor: Samuel Wennek, Wildeburgestrasse 2A, Greifensee (CH), CK-5506

( * ) Notice: Subject to any disclaimer, the term of this patent is extended or adjusted under 35 U.S.C. 154(b) by 0 days.

(21) Appl. No.: 09/432,880

(22) Filed: Nov. 2, 1999

(51) Int. Cl.⁷ ............................................. A61M 11/00
(52) U.S. Cl. ................................... 604/94.01; 604/275
(58) Field of Search ....................... 128/203.28, 204.12, 128/205.13, 205.17, 206.11, 913, 203.22, 200.22; 604/94.01, 275, 276, 279

(56) References Cited

U.S. PATENT DOCUMENTS 2,485,184 A  * 10/1949  Blackman et al. ..... 128/200.22

* cited by examiner

Primary Examiner—Anhtuan T. Nguyen
(74) Attorney, Agent, or Firm—Oppedahl & Larson LLP

(57) ABSTRACT

The invention presented here refers to an appliance (1) for the rinsing of nasal cavities and of paranasal sinuses, with a rinsing mixture (3) and with a vessel (2) for containing and letting flow out the rinsing mixture (3) without overpressure, whereby the appliance (1) has an applicator (4) with an applicator aperture (42) for introducing the rinsing mixture (3) into a nostril, applicator (4) and vessel (2) are connected to one another, applicator (4) and vessel (2) are arranged at an angle of inclination (α) to one another, a rinsing sure level (30) in the vessel (2) is on the height contour of the applicator aperture (42) and the rinsing mixture (3) through the applicator aperture (42) can flow into a nostril and through paranasal sinuses, as soon as the level of the rinsing mixture (30) is on the height contour of the paranasal sinuses.

13 Claims, 5 Drawing Sheets

APPLIANCE FOR RINSING

The invention concerns an appliance with a vessel, an applicator and a rinsing mixture. The appliance is utilized for rinsing nasal cavities and paranasal sinuses. This appliance, the application of the appliance and the procedure for rinsing nasal cavities and paranasal sinuses are defined by the claims.

Known appliances for the introduction of liquids into nasal cavities operate with overpressure. A liquid is squeezed out of a vessel by overpressure and this liquid is spray-injected into nasal cavities. Hereby, as a rule small volumes of liquid are sprayed into the nasal cavities drop by drop.

A first disadvantage consists in the fact, that hereby an unpleasant overpressure in the head builds up, which is unpleasant for the user. A further disadvantages lies in the uncontrolled spray-injecting itself; because, for example, it leads to an undesirable penetration of the liquid into the pharyngeal cavity.

In addition, such appliances are available on the market mainly in small portions, as sealed disposable vessels, etc., and lead to waste.

The invention presented here has an object, which cannot be solved by known appliances. The appliance has the objective of an appliance for rinsing the nasal cavities as well as the paranasal sinuses such as maxillary sinuses and frontal sinuses. The rinsing is to be carried out with significantly greater volumes of liquid that the spray-injection with known devices. The rinsing is to take place in a controlled manner, in particular no water shall penetrate into the pharyngeal cavity in an uncontrolled manner.

This object is solved by the invention in accordance with the claims.

The invention exploits a surprising effect. If one inclines ones head to the side, approximately in such a way, that the two nasal apertures (nostrils) are situated on different height contours to one another and so that the upper one of the nasal apertures is approximately on the same height contour with the maxillary—and frontal sinuses, then opens ones mouth to equalize the pressure and pours a rinsing mixture into a first, upper nostril, then it flows through the maxillary sinuses and frontal sinuses to the further, lower nostril and out from it.

By the controlled posture (head inclined to one side), therefore a controlled flow of a rinsing mixture through nasal cavities and paranasal sinuses is made possible. Made possible in particular is a continuous rinsing of the maxillary sinuses and frontal sinuses in an open circuit. The rinsing takes place without overpressure. The flow of the rinsing mixture is adjusted by the controlled posture of the head (flow through a first upper nostril through the paranasal sinuses to a further lower nostril) and through the height contour of the rinsing mixture level in an appliance utilized for this. (The level of the rinsing mixture of the appliance is on the height contour of the paranasal sinuses). With this method of rinsing, no rinsing mixture undesirably penetrates into the pharyngeal cavity. The flowing of the rinsing mixture takes place solely on the basis of gravity. The rinsing is carried out with larger volumes of rinsing mixture and therefore makes possible a continuous cleaning of the nasal cavities and paranasal sinuses in a flow of rinsing mixture. The rinsing can be carried out without any medical knowledge by anybody, it is a cosmetic application, similar to the cleaning of teeth by means of a toothbrush Foreseen for this rinsing, as stated, is an appliance. The appliance for rinsing consists of a vessel for containing the rinsing mixture and for letting it flow out without overpressure. The rinsing mixture is, for example, a saline solution. The saline solution can be prepared in the vessel, to do this, salt can be dosed into the vessel of the appliance from an (external) storage container and dosed with water: The appliance furthermore has an applicator with an applicator aperture for introducing the rinsing mixture into a nostril. Applicator and vessel are joined together. To be precise, the applicator and the vessel are arranged at an oblique angle to one another, in such a manner, that a rinsing mixture level in the vessel is on the height contour of the applicator aperture. If one applies the appliance with the applicator aperture to a first, upper nostril and brings the rinsing mixture level to the median height contour of the paranasal sinuses (maxillary sinuses and frontal sinuses), then the rinsing mixture flows through the applicator aperture into this upper nostril from it into a first, upper nasal cavity, through a first, upper maxillary sinus adjoining the nasal cavity, from there into an adjoining first, upper frontal sinus, through this upper frontal sinus into an adjoining, lower frontal sinus and from this into an adjoining further, lower maxilary sinus, through this lower maxillary sinus into an adjoining further, lower nasal cavity and from the lower nasal cavity out through the following further, lower nostril. In doing so, it is presumed, that a pressure equalization takes place in the head as a result of the rinsing mixture flowing in by opening the mouth and that in the appliance a pressure equalization takes place because of the rinsing mixture flowing out, for example through an opening for venting the vessel. This procedure for the rinsing of nasal cavities and paranasal sinuses takes place by the application of the appliance in accordance with the invention.

The embodiments of the invention are described in detail on the basis of the following Figures.

Figure 1:
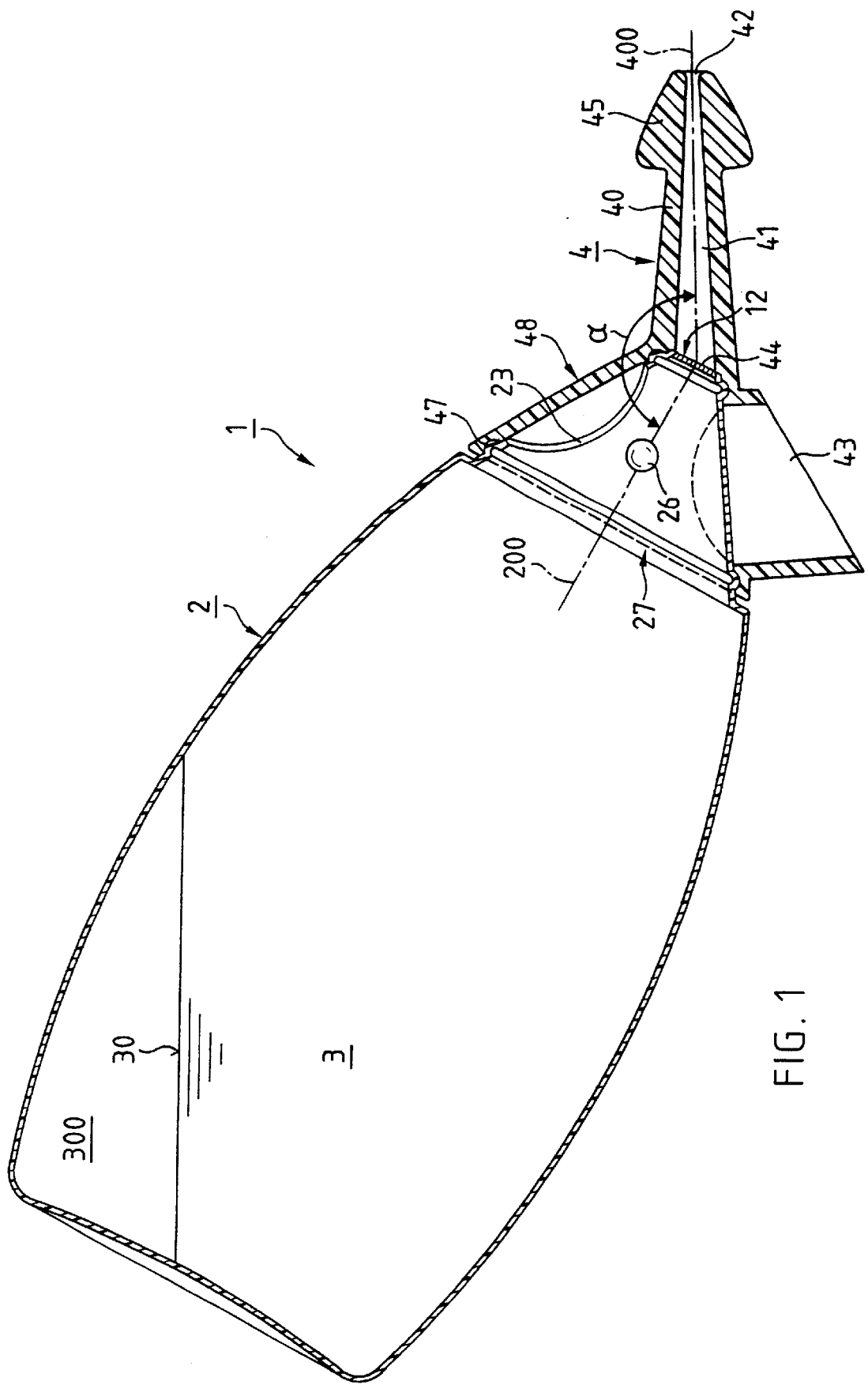
FIG. 1 shows a view through a part of a first preferred embodiment of the appliance in accordance with the invention.

FIG. 1 shows a longitudinal section through a part of a first preferred embodiment of the appliance in accordance with the invention 1. This appliance 1 consists of the vessel 2, which contains the rinsing mixture 3 free of any overpressure and the applicator 4. Within the scope of the invention, it is quite well possible to manufacture the vessel and the applicator as a single part, in preference, however, they are manufactured out of two parts.

Typical materials are plastic and glass. In preferred embodiments the vessel 2 is made of polypropylene and the applicator 4 out of acrylonitrile-butadiene-styrene mould plug copolymer. With knowledge of the invention, of course other materials, such as metal (aluminum, sheet steel, etc.), can be utilized. The vessel 2 can also be collapsible as a space-saving travelling vessel, manifold and diverse possibilities are given. The applicator 4 has an applicator funnel 40 with applicator channel 41 and concluding applicator cap 45 with an applicator aperture 42. Vessel 1 and applicator 4 are connected to one another. A vessel opening 12 of the vessel 1 leads into the applicator channel 41 of the applicator 4. This connection is sealed towards the outside through sealing surfaces in the contact zone around the vessel opening 12 and around the applicator channel 41. Optionally, a particle filter 44 can be placed between vessel opening 12 and the applicator channel 41. The particle filter 44 prevents the ingress of contaminants into the inside of the appliance 1.

The applicator cap 45 concluding the applicator funnel 40 of the applicator 4 is designed in such a manner, that when it is applied to a nostril it closes off this nostril towards the outside like a seal without any pressure having to be applied, it does not obstruct the rinsing mixture 3 flowing into the nostril through the applicator aperture 42, also, however, does not penetrate too deeply into the nostril, which can be unpleasant for the user and can, for example, injure the nasal mucous membrane. In preference, the applicator cap 45 has a shape like a mushroom-head. The geometry can be adjusted to suit small and big nostrils. This applicator cap 45 shaped like a mushroom-head enables a tiling of the appliance 1 applied to a first nostril around this applicator cap 45. In this manner, the rinsing mixture level 30 can be brought to the height contour with respect to the paranasal sinuses, which triggers the rinsing process, and without any rinsing mixture 3 escaping at the sealing applicator cap 45.

The appliance in accordance with the invention 1 in preference has two main axes 200,400 at an angle to one another. The vessel 2 has a main vessel axis 200 along its longitudinal expanse, which main vessel axis 200 is rotationaly symmetrical with respect to the vessel opening 12. The applicator 4 has a main applicator axis 400 along its longitudinal expanse, which main applicator axis 400 is rotationally symmetrical with respect to the applicator aperture 42. The main vessel axis 200 and the main applicator axis 400 are inclined under an angle of inclination α. This angle of inclination α is selected in such a manner, that the geometrical shape of the applicator 4 together with the functionally required geometry of the vessel 2 has an optimum anatomical and functional geometry. The main axes 200,400 are therefore in a multiple operational association, which is expressed by an angle of inclination α. The angle of inclination α amounts to between 0° and 180°. In advantageous embodiments of an appliance 1, the angle of inclination α amounts to approximately 150°.

Figure 4:
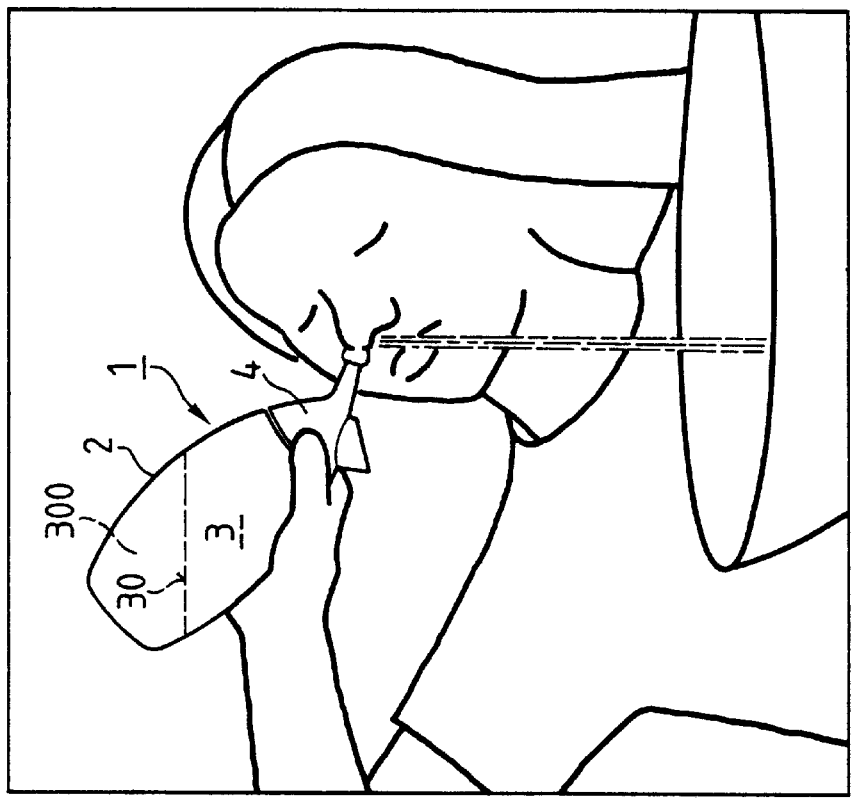
FIGS. 3 and 4 show a view of the application of the appliance in accordance with the invention as a rinser for the rinsing of the nasal cavities and of the paranasal sinuses.
Figure 3:
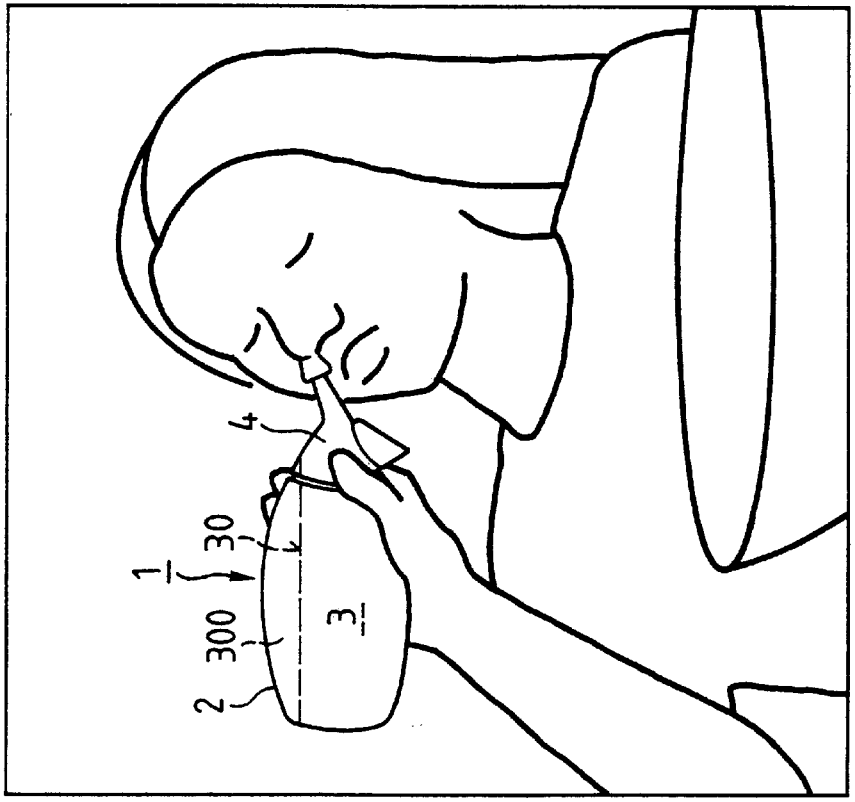

This operational association of the main axes 200,400 shall in the following be explained in an exemplary fashion. Various factors, such as the angle of inclination of the head during rinsing, the circumference and the relative position of the appliance 1 to the head play a role. I.e., how well can the user hold the appliance 1 with one hand during rinsing and in particular how well can he tilt the appliance while holding it against his head. In exemplary procedural steps in accordance with the FIGS. 3 and 4, the main axes 200,400 during the preparation of the rinsing process are tilted by an angle of inclination α of 150° with respect to the horizontal plane of the picture. The position of the horizontal plane of the picture of the FIGS. 3 and 4 is indicated by the level of the rinsing mixture 30. Above the level of the rinsing mixture 30, there is a space free of rinsing mixture 300. This angle of inclination α of 150° is a function of the head inclination of the user (approximately 10° to 20° inclination of the head with respect to the horizontal plane of the picture in the preparatory position in accordance with FIG. 3) and of a holding angle of the appliance 1 during rinsing comfortable for the user (approximately 30° difference to FIG. 3 in the rinsing position in accordance with FIG. 4). Hereby the main axis 400 of the applicator 4 is advantageously slightly turned around the horizontal plane of the picture, from approximately −15° to approximately +15° relative to the horizontal plane of the picture (which is a tilting comfortable for the user, because the applicator cap 45 is seated in a first nostril in a manner producing a seal). And the main axis 200 of this vessel 2 is turned around the applicator cap inserted into a first nostril approximately from 0° to 30° relative to the horizontal plane of the picture (so that the level of the rinsing mixture 30 reaches the height contour with respect to the paranasal sinuses, which triggers the rinsing process). With the knowledge of the invention presented here, the expert of course has a multitude of other possibilities of variation in the implementation of such appliances at his disposal without, however making a new contribution to the invention.

Figure 2:
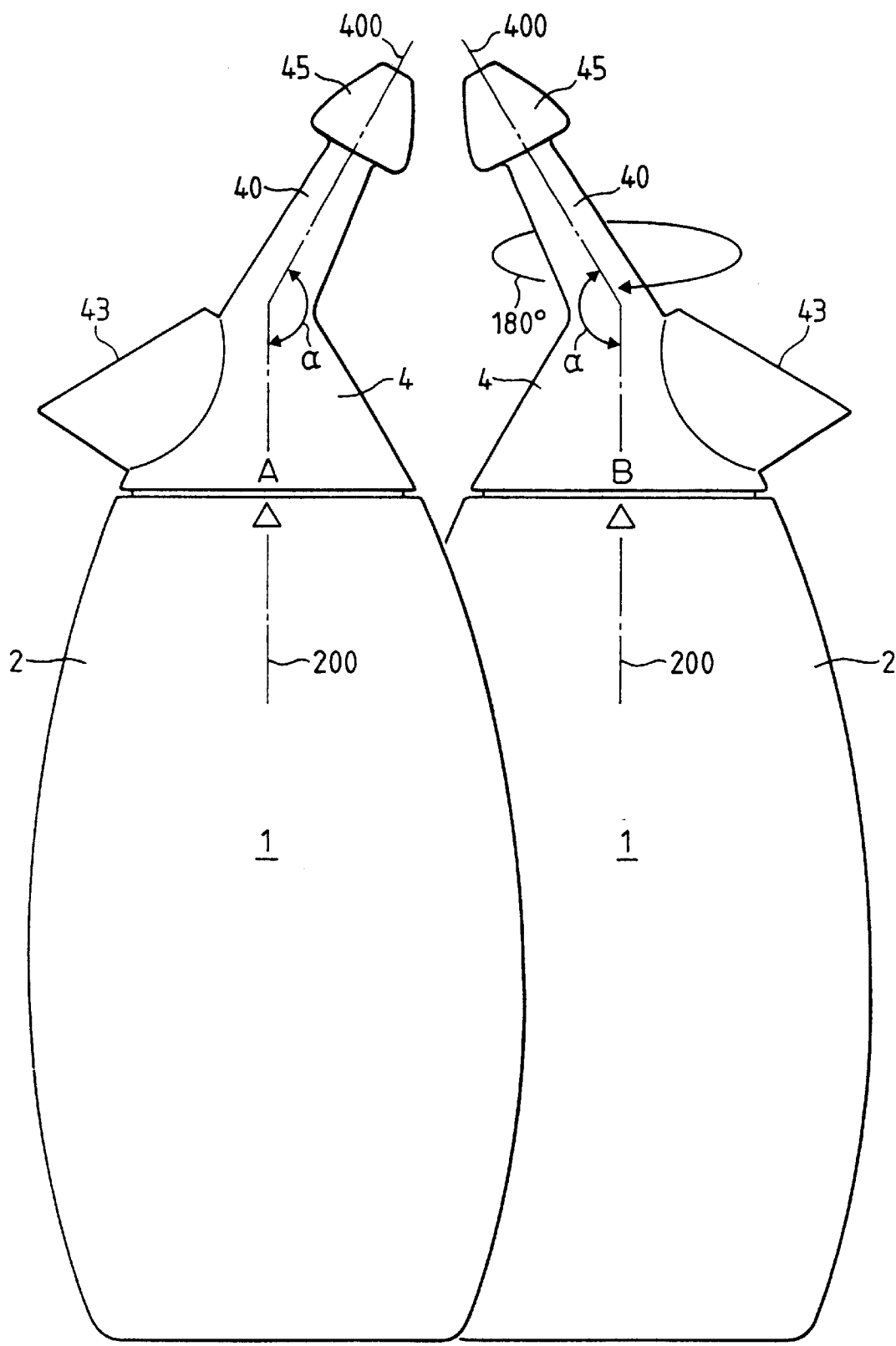
FIG. 2 shows a view of parts of the first preferred embodiment of the appliance in accordance with FIG. 1, on the left in a position with the filling opening open, on the right in a position with the filling opening closed.

In order to make accessible an opening 23 of the vessel 2, the applicator 4 and the vessel 2 are advantageously connected to one another by means of a revolving joint. For example, the applicator 4 of the embodiment of an appliance 1 in accordance with FIG. 1 is connected by means of a wedge-groove mechanism revolving around the main vessel axis 200. Hereby, for example, a circular groove on the inside of the applicator 4 engages in a corresponding vessel coupling 27 on the outside of the vessel 2. The applicator 4 is therefore carried in such a manner relative to the vessel 2, that, for example, two positions A,B of the applicator 4 can be locked relative to the vessel 2. In accordance with FIG. 2 on the left, in a first position A the opening 23 of the vessel 2 is freely accessible through a fill opening 43 of the applicator 4, in accordance with FIG. 2 on the right, this opening 23 of the vessel 2 is in a further position B inaccessibly covered by the applicator 4.

This locking of two positions A,B of the applicator 4 relative to the vessel 2 can be unlocked without requiring greater force through engaging devices. In accordance with FIG. 1, the engaging device, for example, consists of two protrusions 26 of the vessel wall 2 arranged offset to one another by 180°. These protrusions 26 seen from the main vessel axis 200 are protrusions with a ball-shell shape facing outwards. The protrusions 26 in the positions A,B of the applicator 4 relative to the vessel 2 engage indentations located on the inside of the applicator 4, which correspond to the protrusions with a ball-shell shape. With knowledge of the invention presented here, the expert can utilize a multitude of known engaging devices for making accessible the opening 23 of the vessel 2. It goes without saying, that the protrusions could also be located on the applicator 4 and the indentations also on the vessel 2.

The opening 23 of the vessel 2 in a first position A serves for filling the vessel 2 with rinsing mixture 3 and in a further position B it serves for the venting of the vessel 2. In a position A, the fill opening 43 of the applicator 4 is positioned at the opening 23 of the vessel 2, so that rinsing mixture 3 can be filled into the vessel 2 through the fill opening 43 and through the opening 23. Above the rinsing mixture level 30, there is a space 300 free of rinsing mixture. The rinsing mixture 3 is advantageously a 0.9% saline solution. With the knowledge of the invention presented here, however, also other rinsing mixtures (water with herbal salts, tea, etc.) and other concentrations of rinsing mixtures can be utilized. The fill opening 43 of the applicator 4 and the opening 23 of the vessel 2 are with respect to their circumference advantageously dimensioned to be big enough, so that it is possible to pour the salt for the saline solution in an appropriate dosage from a separate storage container into the vessel 2, thereupon to pour in a certain quantity of water to dissolve this salt and to possibly insert a sensor, in order to determine, resp., to check the concentration of the saline solution.

As soon as the rinsing mixture 3 has been filled into the vessel 2, the appliance 1 is secured against any spilling of the rinsing mixture 3 by turning the applicator 4 into a position B.

In this position B, a closed wall section 48 of the applicator 4 is positioned against the opening 23 and seals it off (see FIG. 1). The closed wall section 48 seals off the edges of the opening 23 to such an extent, that rinsing mixture 3 cannot get out through the opening 23, that, however, air can flow into the vessel 2 through the opening 23. Air in particular has to flow into the vessel 2, so that during rinsing, i.e., when the rinsing mixture 3 is flowing out a constant atmospheric pressure (pressure equalization) can be maintained inside the vessel 2. Manifold and diverse methods for venting vessels are known to the expert, so that while no rinsing mixture 3 can escape from the opening 23, air for the venting of the appliance 1 can enter. Above the level of the rinsing mixture 30 there is the space free of rinsing mixtue 300.

Figure 5:
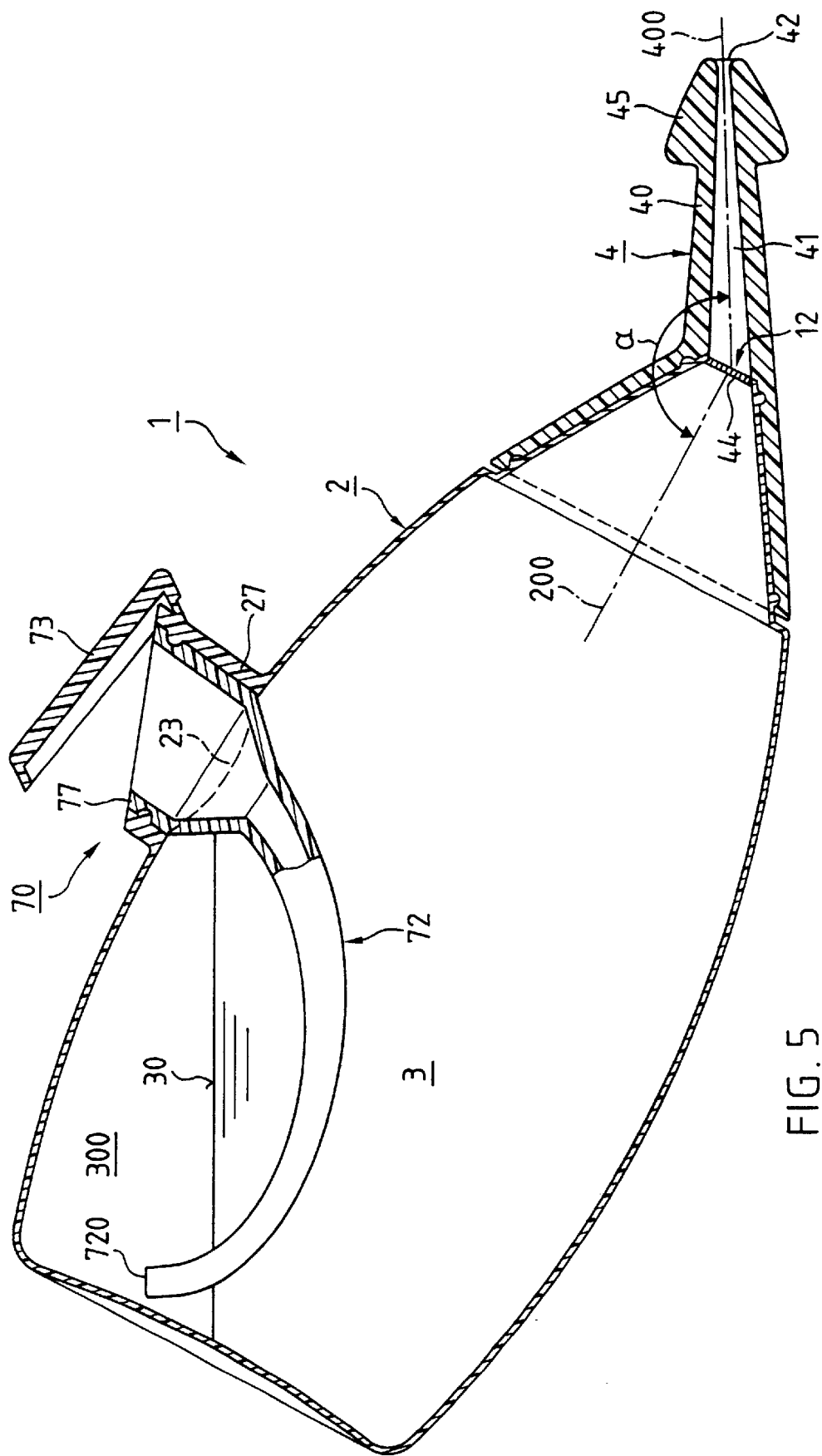
FIG. 5 shows a sectional view through a part of a further preferred embodiment of the appliance in accordance with the invention.

FIG. 5 shows a longitudinal section through a part of a further preferred embodiment of the appliance in accordance with the invention 1. The appliance 1 in accordance with FIG. 5 is to a great extent similar to that of the first embodiment in accordance with the FIGS. 1 and 2, so that reference is made to their description and in the following only differences from this firs embodiment are discussed.

This embodiment of the appliance 1 in accordance with FIG. 5 does not have an applicator 4 fixed to the vessel 2, which can be rotated. The appliance 1 in accordance with FIG. 5 is characterize by an applicator 4 rigidly fixed to the vessel 2 without a fill opening 43. It has a venting device 70 for venting the appliance 1 and in particular the vessel 2. The venting device 70 is connected to a vessel coupling 27 of the vessel 2 through a hose coupling 77. A hose 72 extends into the inside of the vessel 2, hose coupling 77 and vessel coupling 27 delimit an opening 23 in the vessel 2, which can be closed rinsing mixture-tight by a lid 73. The hose coupling 77 can be engaged with the vessel coupling 27 without requiring great force (for example, by pushing in the venting device 70) and released again (for example by pulling out the venting device 70). The venting device 70 is in preference made of the same materials as the vessel 2 and/or the applicator 4.

The opening 23 serves for venting of the vessel 2 and it serves for film the vessel 2 with rinsing mixture 3. In order to fill the vessel 2, the lid 73 is opened and rinsing mixture is filed through the opening 23. During the rinsing process, the lid 73 is preferably closed, so that rinsing mixture 3 cannot escape from the opening 23. The lid 73 seals the edges of the opening 23 to such an extent, that rinsing mixture 3 cannot get out through the opening 23, that air, however, can flow into the vessel 2 through the opening 23. Air in particular has to flow into the vessel 2, so that during rinsing, i.e., while the rinsing mixture 3 is flowing out, it can maintain a constant atmospheric pressure inside the vessel 2 (pressure equalization). The expert is familiar with many and diverse devices for venting vessels.

Figure 6:
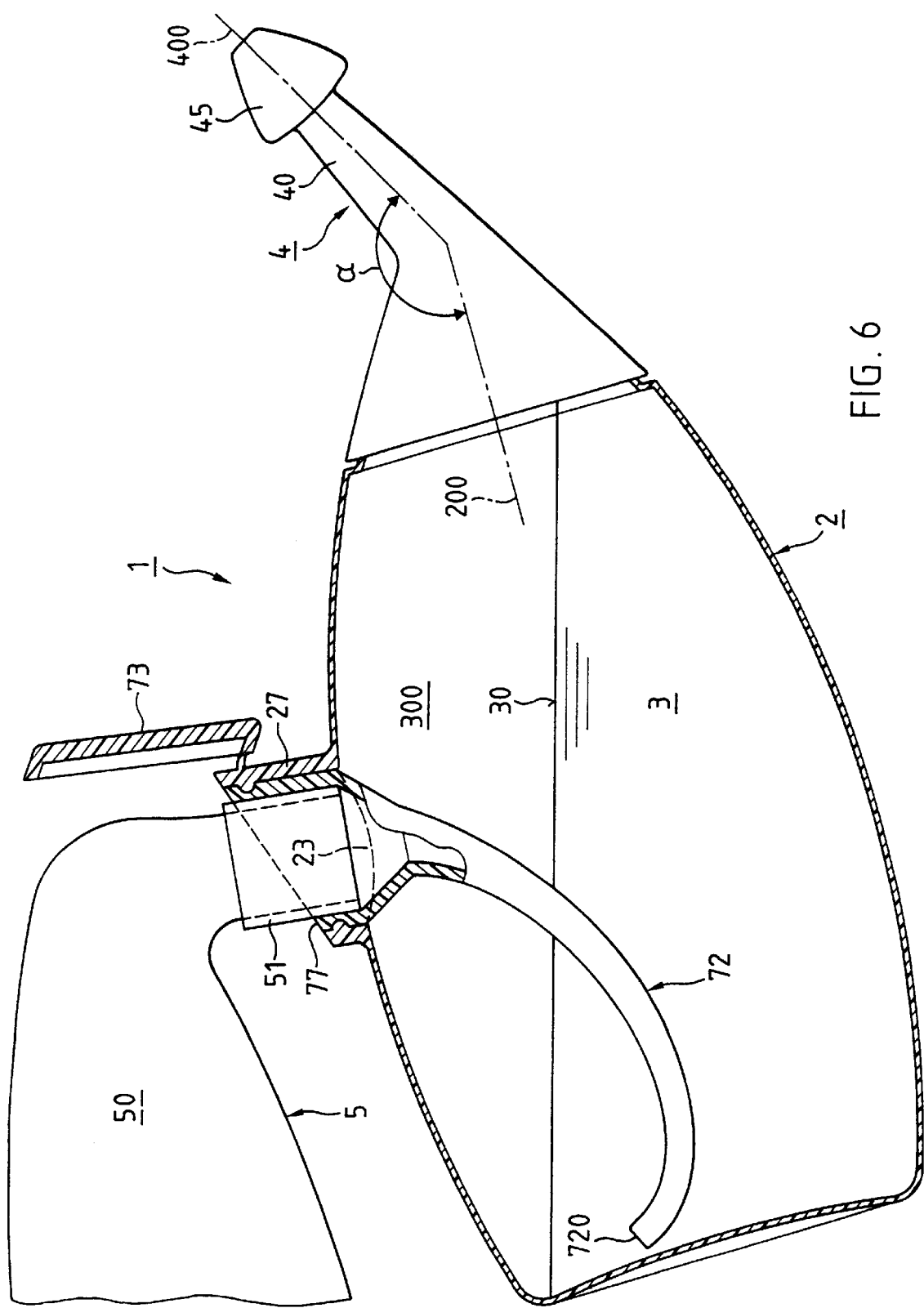
FIG. 6 shows a sectional view through a part of a further preferred embodiment of the appliance in accordance with the invention.

The hose 72 is curved in such a manner, that one end of the hose 720 of the appliance 1 in the rinsing position (angle of inclination $\alpha=150°$) extends into the space free of rinsing mixture 300 above the rinsing mixture level 30, so that in accordance with FIG. 6 a venting of the vessel 2 takes place through the hose 72 and not through the rinsing mixture 3. During venting, any rinsing mixture 3 in the hose 72 is sucked into the vessel 2 like a funnel as a result of a suction effect. This is a difference to the first embodiment of the appliance 1, where the venting of the vessel 1 in the rinsing position (angle of inclination $\alpha=150°$) takes place from the venting opening 23 below the level of the rinsing mixture 30 through the rinsing mixture 3 by means of air bubbles. (see FIG. 1). The advantage of the further embodiment in accordance with FIG. 6 consists of a venting without any bubbles, which leads to a more regular pressure equalization in the appliance 1 and to a particularly regular, homogeneous flow of the rinsing mixture during the application.

FIG. 6 shows a longitudinal section through a part of a further preferred embodiment of the appliance 1 in accordance with the invention. The appliance 1 in accordance with FIG. 6 is to a great extent similar to the first embodiment in accordance with FIGS. 1 and 2 as well as to that of a further embodiment in accordance with FIG. 5, so that reference is made to their description and in the following only differences from these embodiments are discussed.

In the further embodiment of an appliance 1 in accordance with FIG. 6, a refill pack 5 with refill rinsing mixture 50 is mounted with a tight fit on the opening 23 of the appliance 1 with a refill funnel 51. In comparison with the embodiment of an appliance 1 in accordance with FIG. 5, the lid 73 is flipped back The refill pack 5 can, even if this is not explicitly illustrated, also be mounted with a tight fit to an opening 23 of the embodiment of an appliance 1 in accordance with the FIGS. 1 and 2. In this case, the applicator 4 is in the first position A for filling the vessel 2.

Within the scope of the invention presented here, it is foreseen, not, however, explicitly shown in the Figures, that when mounting the refill funnel 51 on the opening 23 of the appliance 1, a sealing diaphragm of the refill pack 5 is automatically perforated and torn open, and that the refill rinsing mixture 50 contained in it is filled into the vessel 2 through the hose 72 by squeezing the flexible refill pack 5. The venting of the appliance 1 during refilling with this refill pack 5 takes place through the applicator aperture 42. With knowledge of the invention presented here, the expert has manifold and diverse variations of such refill procedures at his disposal.

I claim:

1. An appliance for rinsing nasal cavities and paranasal sinuses, comprising a vessel for containing a rinsing mixture and letting the rinsing mixture flow out without overpressure, the vessel having a main vessel axis with a bottom without openings on one side of the vessel and a vessel opening at the opposite side of the bottom, the appliance further comprising an applicator with an applicator aperture defining a main applicator axis, the applicator being for introducing the rinsing mixture into a nasal aperture (nostril), the applicator being connected to the vessel at the side of the vessel opening, the applicator defining an angle of inclination, so that when the applicator is connected with the vessel, there is an angle of inclination between the main vessel axis and the main applicator axis, wherein the vessel has an opening, the applicator has a fill opening and a closed wall section, the applicator and the vessel are arranged so that they can rotate relative to one another, and the opening is arranged with respect to the fill opening, such that in a first position of the applicator, the fill opening is positioned in front of the opening, and that in a further position the closed wall section is positioned in front of the opening.

2. The appliance according to claim 1 wherein the vessel has rotationally symmetrical shape.

3. The appliance according to claim 1 wherein the applicator and the vessel are arranged so that they can rotate relative to one another.

4. The appliance according to claim 1, wherein the applicator can rotate around the main vessel axis of the vessel.

5. The appliance according to claim 1, wherein the bottom is shaped such that the appliance can stand on its bottom.

6. The appliance according to claim 1, wherein the appliance comprises means to lock the applicator relative to the vessel in at least two positions.

7. The appliance according to claim 1, wherein the vessel in the first position can be filled with rinsing mixture through the fill opening, and that the vessel in the further position with the closed wall section seals off the edges of the opening against rinsing mixture so that rinsing mixture does not escape from the vessel through the opening, so that air, however, can flow into the vessel through the opening for equalizing pressure.

8. The appliance according to claim 1 further comprising an opening so that air can flow into the vessel, so that a continuous flow of rinsing mixture can flow through the applicator aperture.

9. The appliance according to claim 1, wherein the main axis of the applicator has an angle of inclination of 150° relative to the main axis of the vessel.

10. The appliance according to claim 9, wherein the angle of inclination is such that an applicator cap can be inserted in a first nostril in a manner producing a seal, and and wherein by tilting the appliance around the inserted applicator cap the level of the rinsing mixture can be brought on to the height contour relative to the paranasal sinuses, which triggers the rinsing process.

11. The appliance according to claim 1, wherein the applicator and the vessel are arranged rigidly relative to one another, and that a venting device is connected to the vessel, that a hose extends inside the vessel from an opening of the vessel and that a lid seals the opening against rinsing mixture, so that rinsing mixture does not come out of the vessel through the opening, so that air can, however, flow into the vessel through the opening through the hose for equalizing the pressure.

12. The appliance according to claim 1, wherein the rinsing mixture is a saline solution.

13. The appliance according to claim 8, wherein the opening is adapted to be connectable with a refill funnel of a refill pack.

* * * * *